(12) United States Patent
Wilk et al.

(10) Patent No.: US 6,231,496 B1
(45) Date of Patent: May 15, 2001

(54) MEDICAL TREATMENT METHOD

(76) Inventors: Peter J. Wilk, 185 W. End Ave., Unit 22M, New York, NY (US) 10023; Mitchell N. Essig, 227 High Brook Ct., Pelham, NY (US) 10803

( * ) Notice: Subject to any disclaimer, the term of this patent is extended or adjusted under 35 U.S.C. 154(b) by 0 days.

(21) Appl. No.: 09/349,003

(22) Filed: Jul. 7, 1999

(51) Int. Cl.[7] .................................................. A61B 17/52
(52) U.S. Cl. .............................................. 600/9; 128/898
(58) Field of Search .......................... 128/898; 607/103, 607/100, 101; 600/9–15

(56) References Cited

U.S. PATENT DOCUMENTS

| | | | |
|---|---|---|---|
| 4,136,695 | * | 1/1979 | Dafoe ................................... 128/215 |
| 4,197,846 | * | 4/1980 | Bucalo ................................... 604/51 |
| 4,795,438 | | 1/1989 | Kensey et al. . |
| 4,983,159 | * | 1/1991 | Rand ........................................ 600/9 |
| 5,043,101 | * | 8/1991 | Gordon .............................. 252/408.1 |
| 5,061,267 | | 10/1991 | Zeiher . |
| 5,336,205 | | 8/1994 | Zenzen et al. . |
| 5,558,673 | * | 9/1996 | Edwards et al. ........................ 606/41 |
| 5,693,080 | | 12/1997 | Wallsten et al. . |
| 5,697,948 | * | 12/1997 | Marin et al. ........................... 606/198 |
| 5,769,879 | * | 6/1998 | Richards et al. ...................... 607/101 |
| 5,921,244 | | 7/1999 | Chen et al. . |

\* cited by examiner

*Primary Examiner*—Linda C. M. Dvorak
*Assistant Examiner*—R Kearney
(74) *Attorney, Agent, or Firm*—R. Neil Sudol; Henry D. Coleman

(57) ABSTRACT

In a sterilization method a plethora of magnetizable metal particles are deposited into a uterus of a living female organism. Subsequently, a magnet is placed near an external skin surface of the female organism near the uterus to thereby cause at least some of the metal particles to embed in a myometrium or endometrium of the uterus. The metal particles may be magnetized prior to deposition in the uterus. The particles are advantageously formed to have a sharp end which easily penetrates into the uterine lining. Each particle is magnetized so that the sharp end has a predetermined magnetic pole, whereby a magnet with the opposite pole placed against the organism results in an embedding of the sharp end in the uterine lining. In addition, microwave radiation is optionally transmitted into the female organism in a region about the uterus after the embedding of the metal particles in the myometrium or endometrium.

21 Claims, 5 Drawing Sheets

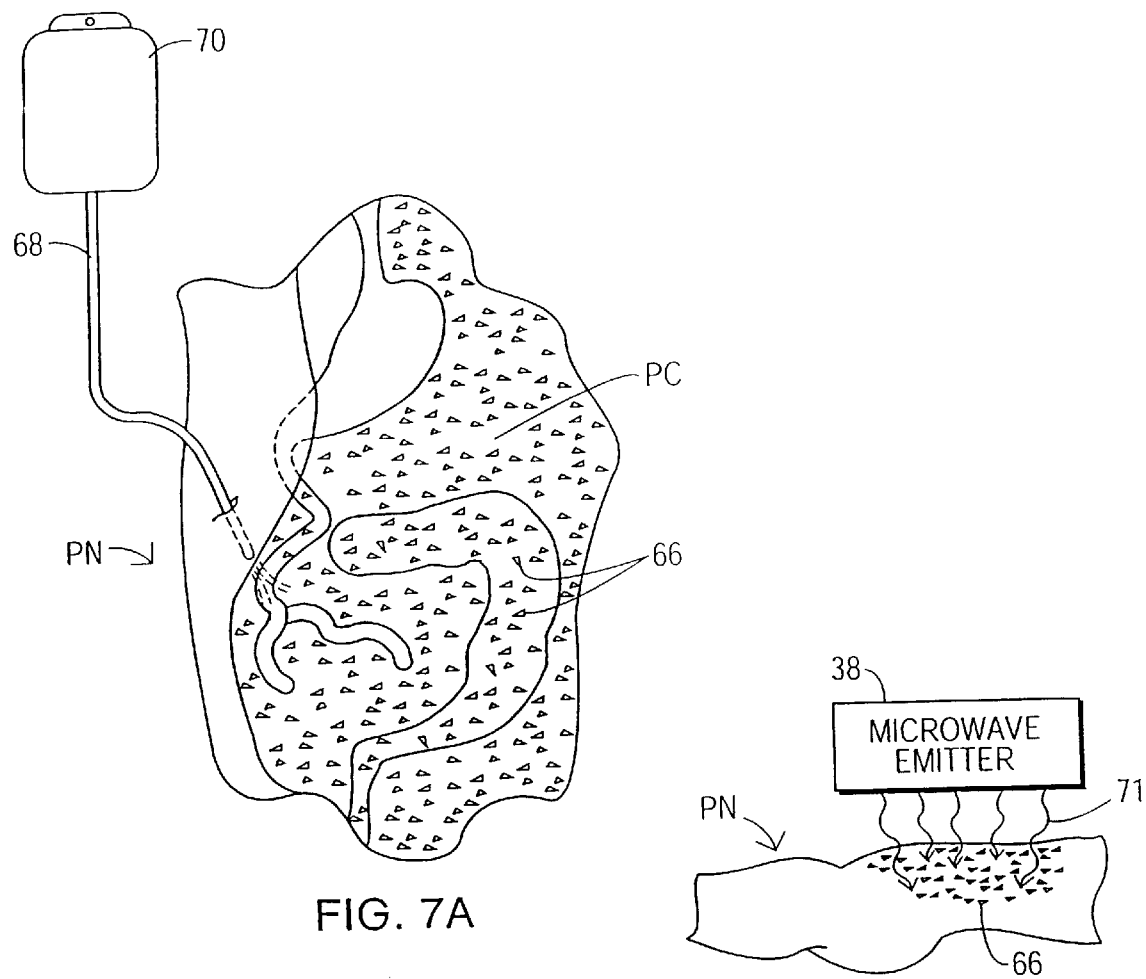
FIG. 7A
FIG. 7B
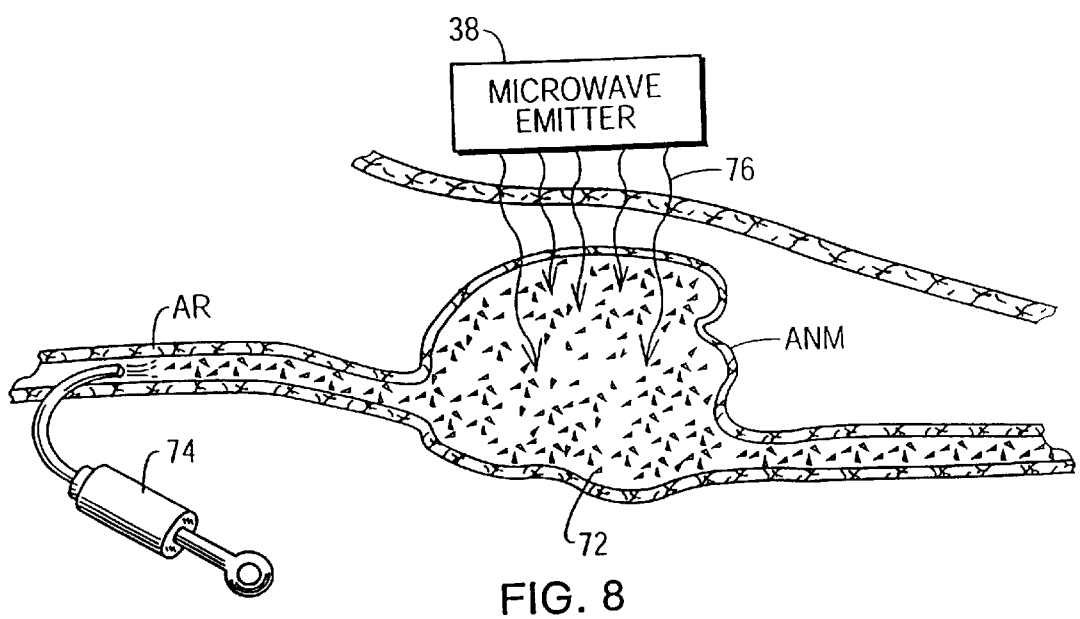
FIG. 8

MEDICAL TREATMENT METHOD

BACKGROUND OF THE INVENTION

This invention relates to a medical treatment method. More particularly, this invention relates to a minimally invasive technique for treating internal tissues of an organism or patient. The technique is especially useful for sterilization of female organisms, as well as in the treatment of at least certain kinds of cancer.

The ever increasing population of human beings has been a topic of scientific reports and substantial media speculation. In many parts of the world, conventional birth control devices or prophylactics are either not available or not used. Such countries tend to have burgeoning citizenries sharing ever decreasing natural resources and other types of wealth. In times past, the increasing demand for reduced fundamentals of life has given rise to war and to other forms of disaster such as famine and disease.

The world is in need of a birth control technique which is inexpensive and easy to implement. Many conventional birth control techniques such as intrauterine devices and vasectomies require a hospital operation. Such operations can be performed only by highly trained personnel. The operations are expensive and time consuming. Consequently, the operations are not available to large segments of the world's population.

OBJECTS OF THE INVENTION

An object of the present invention is to provide a new birth control technique.

Another object of the present invention is to provide such a birth control technique which is simple to use and can be used by personnel of minimally training.

It is a further object of the present invention to provide such a technique or method which is inexpensive.

An additional object of the present invention is to provide such a technique or method which has a high probability of success in preventing unwanted pregnancies.

Yet another object of the present invention is to provide a method for treating internal tissues such as those affected by cancer.

These and other objects of the present invention will be apparent from the drawings and descriptions herein.

SUMMARY OF THE INVENTION

A sterilization method comprises, in accordance with the present invention, depositing a plethora of magnetizable metal particles into a uterus of a living female organism and placing a magnet near an external skin surface of the female organism near the uterus to thereby cause at least some of the metal particles to embed in a lining (myometrium, endometrium) of the uterus.

The metal particles may be magnetized prior to deposition in the uterus. The particles are advantageously formed to have a sharp end which easily penetrates into the uterine lining. Each particle is magnetized so that the sharp end has a predetermined magnetic pole, whereby a magnet with the opposite pole placed against the organism results in an embedding of the sharp end in the uterine lining. The generation of a magnetic field in the uterus via the externally positioned magnet serves not only to orient the metal particles with respect to the uterine lining but also to pull the particles into the lining.

The metal particles advantageously have a tapered form, with an enlarged end opposite the sharp end. The larger end serves to limit the extent to which the metal particles are pulled into the uterine lining.

In accordance with another feature of the present invention, the depositing of the metal particles is accomplished by inserting a tubular member through a cervix of the female organism and injecting the metal particles through the tubular member.

Where the metal particles are suspended in a flowable matrix, the depositing of the metal particles in the uterus includes exerting pressure on the flowable matrix to cause the flowable matrix with the suspended metal particles to flow into the uterus. The exerted pressure forces the flowable matrix with the suspended metal particles through the tubular member after the placement of a distal tip thereof in the uterus of the subject.

In accordance with a further feature of the present invention, the tubular member is provided with a balloon. In that case, the sterilization method further comprises inflating the balloon after inserting the tubular member through the cervix and prior to injecting of the metal particles through the tubular member. The inflated balloon serves to close the uterus to retain the metal particles in the uterus.

Pursuant to an additional feature of the present invention, the method further comprising emitting microwave radiation into the female organism in a region about the uterus after the embedding of the metal particles in the lining. The strength of the microwave radiation is sufficiently great to cause significant tissue heating and possibly limited electrical discharge in the uterine lining region, thereby advancing the effective destruction of the lining to prevent embryo attachment and gestation. However, the strength of the microwave radiation is insufficient to significantly warm the tissues of the organism outside of the uterine lining.

A sterilization procedure pursuant to the present invention may be performed by personnel with a modicum of training and skills. The sterilization procedure does not require expensive or complicated equipment or instruments. A solution or suspension of metal particles, an injection tube, and a magnet are all that's necessary. Even the optional microwave generator is conventional technology which is easy to use. The magnet may be a permanent magnet or an electromagnet. The injection tube may be provided with a balloon for holding the metal particles in the uterus during the embedding thereof in the uterine lining.

Where the organism is human, it may be best to have the patient disposed stomach down in the Trendelenburg position during at least part of the sterilization procedure.

The metal particles may be coated with a biological irritant composition to cause scarring of the lining after embedding of the metal particles in the lining.

A medical treatment method comprises, in accordance with the present invention, (a) depositing a plethora of magnetizable metal particles into internal tissues of a living organism and (b) emitting microwave radiation into the organism in a region about the internal tissues after the depositing of the metal particles in the internal tissues.

Where the internal tissues are a lining, the depositing of the metal particles includes inserting a tubular member through a skin surface of the organism and into a cavity defined or surrounded by the lining and further includes filling the cavity with a solution or suspension containing the metal particles. The lining may be a peritoneal lining, and the cavity a peritoneal cavity.

Where the internal tissues are a tumorous growth, the depositing of the metal particles includes inserting a hypodermic needle through a skin surface of the organism and into the tumorous growth and additionally includes injecting the metal particles through the needle into the tumorous growth.

A more general method for sterilizing a female comprises, in accordance with the present invention, inserting a tubular member through a cervix of a female organism and thereafter injecting a sclerosing agent into a uterus of the female organism through the tubular member. The sclerosing agent may include a plethora of metal particles, in which case the method further comprises acting on the metal particles to embed the metal particles in a lining of the uterus. The acting on the metal particles generally includes orienting the particles, for example, by applying a magnetic field to the metal particles. As discussed above, microwave radiation is optionally emitted into the female organism in a region about the uterus after the injecting of the metal particles into the uterus.

Other kinds of sclerosing agents include chemical irritants which cause a scarring of the uterine tissues, thereby rendering the uterus incapable of supporting a fetus. Chemical sclerosing agents include salicylic acid solutions and concentrated sugar solutions, for example, a 25–50% dextrose solution. Other known sclerotic agents can also be used. For example, 5% quinine and urea hydrochloride solution. Preferably, the sclerotic agent is a natural substance which is generally nontoxic and biocompatible. A sugar such as dextrose is such a substance. The adhesive agent cyanoacrylate is another such substance.

A sterilization method in accordance with the present invention is equivalent to a tubal ablation. The method is simple to execute: the method can be reliably used by minimally trained personnel. The method is inexpensive: the treatment personnel may be paid at a low rate and the materials and equipment are basic. The method has a high probability of success in preventing unwanted pregnancies.

A method for treating internal tumors and cancerous tissues in accordance with the present invention is also easy to carry out and relatively inexpensive.

BRIEF DESCRIPTION OF THE DRAWINGS

FIGS. 7A and 7B are partial schematic perspective views of a patient's abdomen and instrumentation, showing successive steps in another cancer treatment procedure in accordance with the present invention.

FIG. 8 is a partial schematic perspective view of a patient and instrumentation, showing successive steps in a procedure for treating an aneurysm in accordance with the present invention.

DESCRIPTION OF THE PREFERRED EMBODIMENTS

Figure 1:
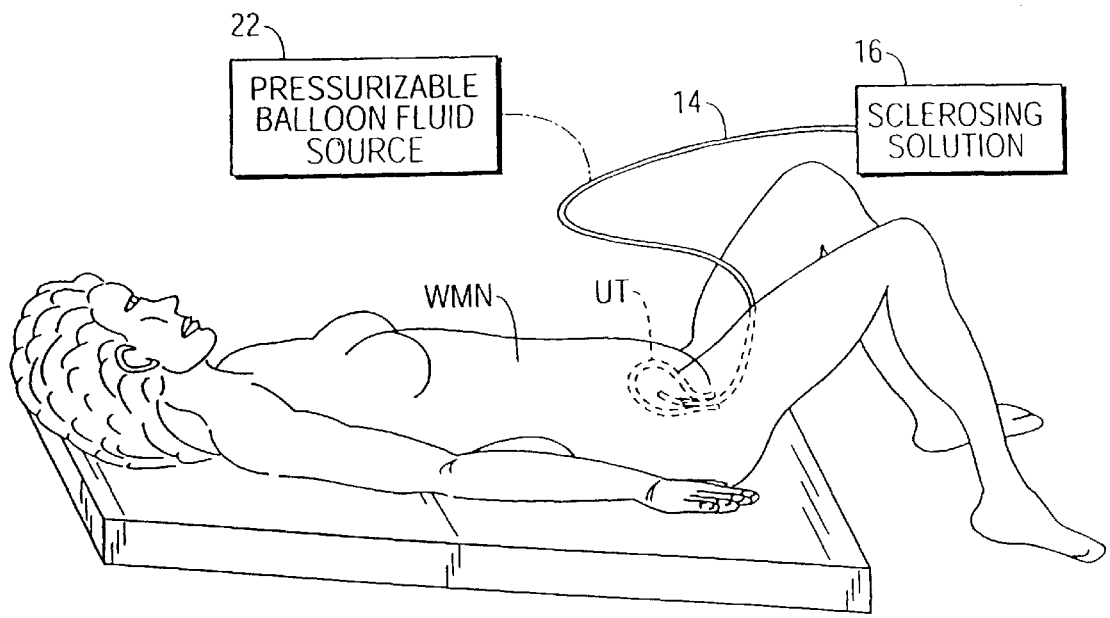
FIG. 1 is partially a block diagram of medical instrumentation and partially a schematic perspective view of a woman being treated in a sterilization procedure in accordance with the present invention, showing the woman's uterus in phantom lines.

As illustrated in FIGS. 1 and 2, a woman or female patient WMN wishing to be sterilized is placed in stirrups (not shown) and has a distal end 12 of a tubular member or catheter 14 inserted through her cervix CX into her uterus UT. A sclerosing solution is fed through tubular member 14 from a reservoir or pressurizable source 16, such as a syringe, into the woman's uterus UT. The sclerosing agent may be a chemical irritant which causes a scarring of the uterine tissues, particularly the myometrial lining or endometrium, thereby rendering the uterus UT incapable of supporting a fetus. Preferably, the sclerotic agent is a chemical substance which is generally nontoxic and biocompatible. The adhesive agent cyanoacrylate is such a substance. Other chemical sclerosing agents include a 5% quinine and urea hydrochloride solution. Salicylic acid solutions and concentrated sugar solutions, for example, a 25–50% dextrose solution are also suitable as sclerosing agents.

The sclerosing agent is maintained in uterus UT for a period of time sufficient to induce myometrial scarring effective to prevent pregnancy. Generally, several minutes are required, the exact minimum varying depending on the particular sclerosing agent and its concentration. After lapse of sufficient time, the uterus UT may be flushed with an irritant and excess sclerosing agent removed via suction, as discussed below.

Where the sclerosing agent takes the form of a solution or slurry or suspension, tubular member of catheter 14 is provided near its distal end 12 with a balloon closure element 20. After insertion of distal end 12 and balloon 20 in a collapsed configuration into uterus UT through cervix CX (FIG. 2A), balloon 20 is inflated by operation of a pressurizable source 22 (FIGS. 1 and 2B) of a fluid such as a saline solution. Upon inflation, balloon 20 is seated at cervix CX and seals the uterus UT from a premature egress of sclerosing solution.

In further discussion with reference to FIGS. 2A–2E, the sclerosing agent is taken to include a plethora of metal particles or filings 18, preferably suspended in a slurry or other flowable matrix 24 such as an aqueous solution or a gel. Metal particles 18 are made of a magnetic or magnetizable material.

Figure 2A:
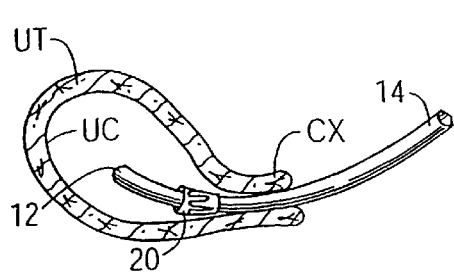
FIGS. 2A–2E are schematic cross-sectional views of the uterus of FIG. 1, showing successive steps in the sterilization procedure with selected instrumentation indicated in block diagram form.
Figure 2B:
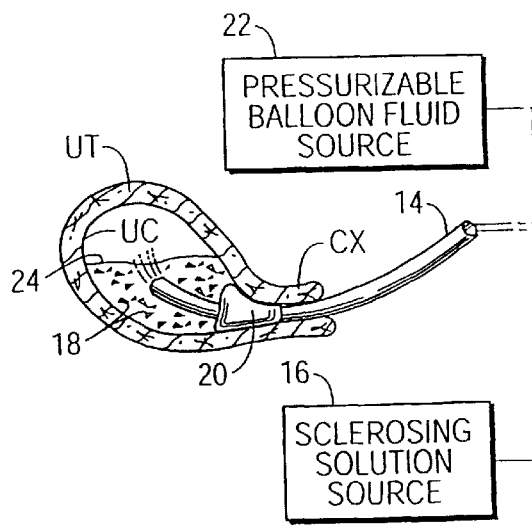
Figure 2C:
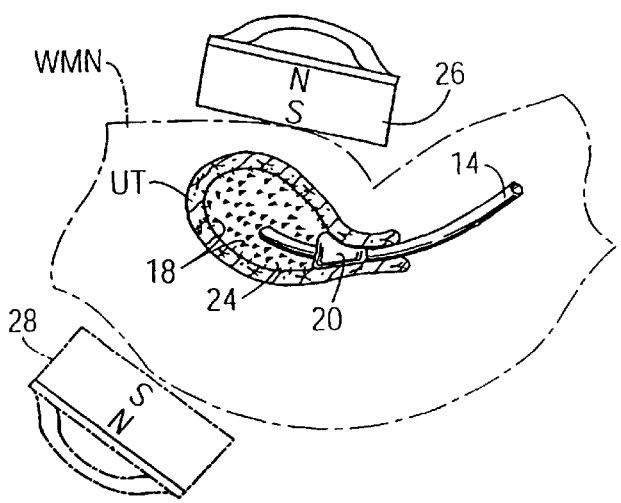
Figure 2D:
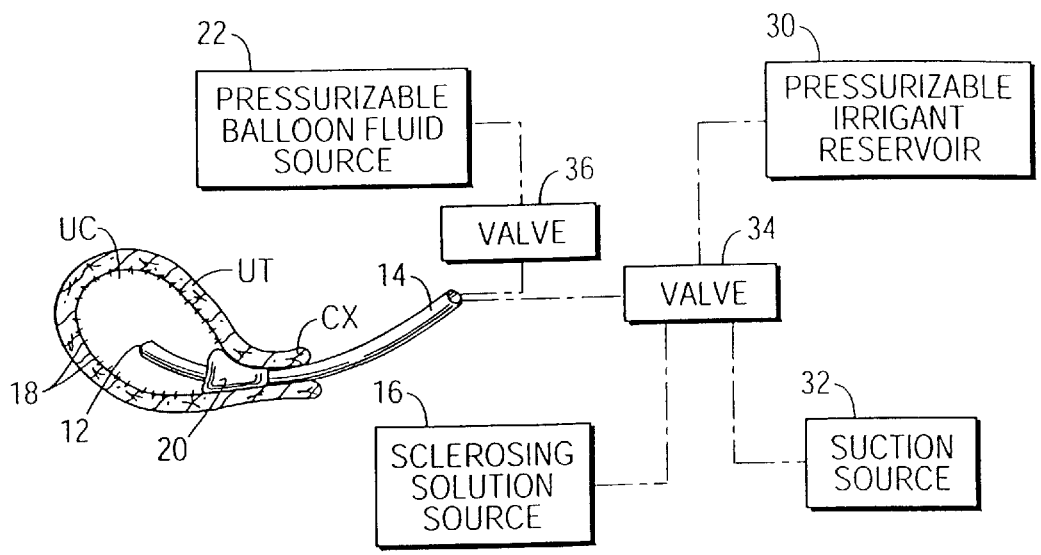

FIG. 2B shows uterus UT partially filled with the suspension or slurry 24 of metal particles 18, which has been injected into uterus UT from source 16. After an effective filling of the uterine cavity UC (FIGS. 2A and 2B) with suspension or slurry 24, a strong magnetic field is generated in the region of uterus UT by placing a permanent magnet 26, for example, of the rare earth kind, or an electromagnet near the uterus. The magnetic field produced by magnet 26 serves to orient metal particles 18 and to pull the particles into the uterine lining, i.e., the myometrium or endometrium (not separately shown). Magnet 26 may be subsequently placed at another location 28 next to the patient WMN to assist in embedding metal particles 18 in another portion of the myometrium or endometrium.

After the embedding of metal particles 18 in the myometrium or endometrium or uterus UT, the suspension or slurry 24 is removed from uterine cavity UC. This removal may be facilitated by additional equipment illustrated in FIG. 2D and including a pressurizable reservoir 30 of a liquid irritant and a suction source 32. After the embedding of metal particles 18, a valve 34 is actuated to connected suction source 32 to tubular member 14, thereby drawing suspension or slurry 24 from uterine cavity UC. Thereafter, valve 34 may be actuated to connect reservoir 30 to uterine cavity UC via tubular member 14. Liquid irritant from reservoir 30 is injected into uterine cavity UC for purposes of washing out free or nonembedded metal particles 18. Valve 34 and suction source 32 are subsequently operated to draw the irritant and loose metal particles 18 from uterine cavity UC. Then, fluid source 22 is depressurized to enable an egress of fluid from balloon 20 and an extraction of the balloon and distal end 12 of tubular member 14 from uterus UT via cervix CX. Fluid source 22 is optionally connected to tubular member 14 via a valve 36 for facilitating the inflation and deflation of balloon 20.

Figure 2E:
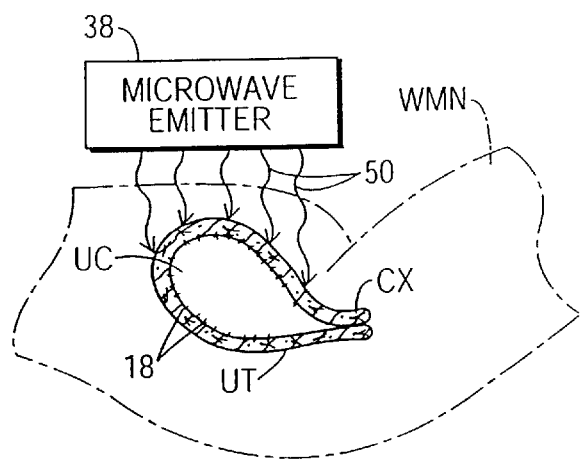
Figure 3:
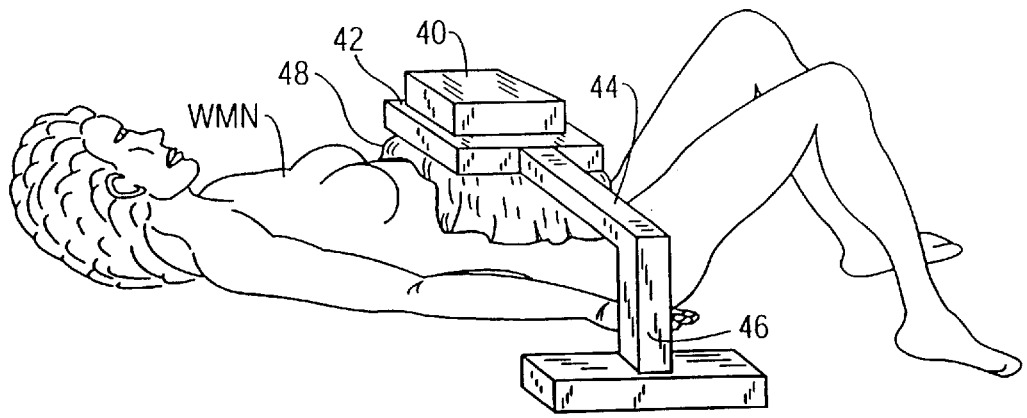
FIG. 3 is a schematic cross-section view similar to FIG. 1, showing a microwave apparatus illustrated in block diagram form in FIG. 2E.

As depicted in FIG. 2E, after the extraction of slurry 24 and renegade metal particles 18 from uterus UT, a microwave emitter 38 is placed adjacent to patient WMN in the area of uterus UT. As illustrated in FIG. 3, microwave emitter 38 may be enclosed in a housing 40 which is supported on a platform or table 42 in turn carried on an arm 44 extending from a post 46. A microwave shield 48 in the form of a skirt is suspended from platform or table 42. In addition, the patient WMN may rest on another microwave shield (not shown) in the form of a pad.

Microwave emitter 38 is designed to generate and emit weak microwave energy 50 for purposes of energizing the metal particles 18 embedded in the myometrium or endometrium of uterus UT. The energized metal particles are heated and create tiny electrostatic discharges in the myometrium or endometrium of uterus UT, thereby quickly and controllably damaging those tissues to result in scarring which effectively prevents future pregnancies. The microwave energy 50 produced by emitter 38 and transmitted into patient WMN is so weak as to prevent significant heating of organic tissues of the patient WMN and yet strong enough to result in energy absorption by embedded metal particles 18. The strength of the microwave energy 50 generated by emitter 38 is less the strength of the energy generated by a consumer-type microwave oven. Preferably, the maximum rate of energy production by emitter 38 is less than half of the lowest rate of energy generation by a conventional consumer-type microwave oven.

The transmission of microwave energy into the patient WMN towards uterus UT is optional. The mere embedding of metal particles 18 in the uterine lining is sufficient to cause scarring which will prevent pregnancy. However, the use of microwave emitter 38 will induce substantially immediate scarring, whereas scarring by the mere embedding of metal particles will be delayed.

Figure 4:
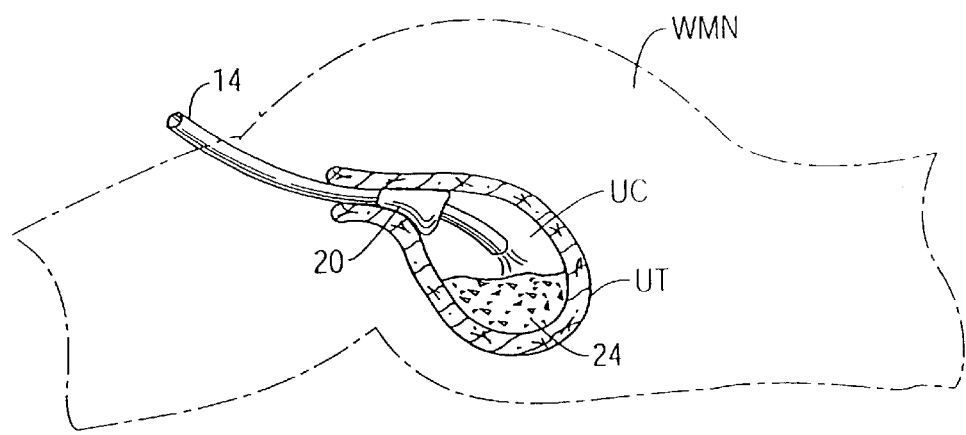
FIG. 4 is a schematic cross-sectional view of a uterus, showing an alternate step in a sterilization procedure in accordance with the present invention.

As illustrated in FIG. 4, patient WMN may be disposed in the Trendelenburg position (face down) for one or more of the steps described above with reference to FIGS. 2A–2E. The patient WMN may be placed in the Trendelenburg position before or after the injection of suspension or slurry 24 into uterine cavity UC.

Figure 5:
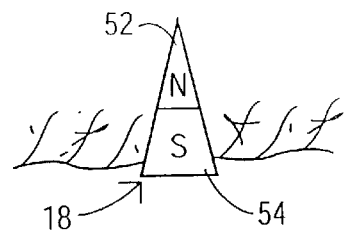
FIG. 5 is a schematic side elemental view, on an enlarged scale, of a magnetic filing or element used in a sterilization procedure in accordance with the present invention.

FIG. 5 depicts a particular configuration for metal particles 18. Each metal particle 18 has a tapered configuration (e.g., wedge-shaped or conical) with a narrow or pointed end 52 and a wide end 54 opposite thereto. Moreover, each particle 18 is magnetized, generally through magnetic induction upon the juxtaposition of magnet 36 to patient WMN, so that ends 52 and 54 exhibit different magnetic poles N and S. Narrow or pointed end 52 will naturally exhibit a magnetic pole opposite to that of the near side of magnet 26 (see FIG. 2C), thereby facilitating embedding of the metal particle in the myometrium or endometrium of uterus UT. The wider end 54 of metal particles 18 may be provided with a flange (not illustrated) as an additional impediment to embedding of the particles too deeply in the myometrium or endometrium.

Figure 6A:
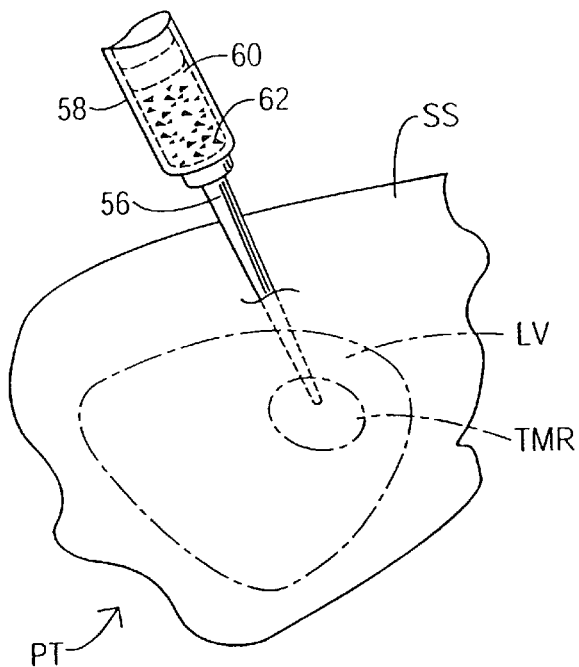
FIGS. 6A and 6B are partial schematic perspective views of a patient's abdomen and instrumentation, showing successive steps in a related cancer treatment procedure in accordance with the present invention.
Figure 6B:
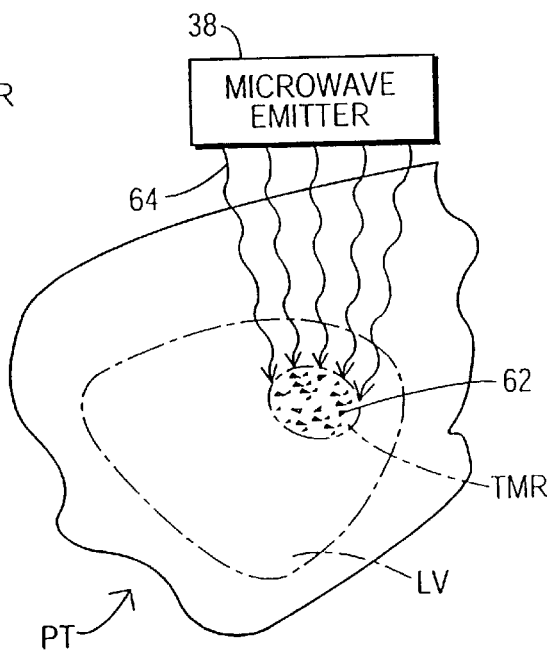

The technique of microwave energization of metal particles discussed above may be applied in other kinds of treatment. For example, as illustrated in FIG. 6A, a needle 56 of a syringe 58 holding a suspension or slurry 60 of metal particles 62 may be inserted through a skin surface SS of a patient PT into an inoperable tumor TMR in the patient's liver LV and actuated to inject suspension or slurry 60 with metal particles 62 into the tumor. Subsequently, as shown in FIG. 6B, microwave emitter 38 is juxtaposed to the patient PT and energized to transmit low-energy microwave radiation 64 into the patient. The low-energy microwave radiation 64 is absorbed mainly by the injected metal particles 62 to cause a localized heating and sparking in tumor TMR, thereby destroying the tumor cells.

In another application schematically illustrated in FIGS. 7A and 7B, a suspension or slurry of metal particles 66 is fed through a catheter 68 from a bag or pouch 70 into a peritoneal cavity PC of a patient PN having diffuse peritoneal tumor seeding. As discussed above, a magnet is optionally used in some cases to embed the metal particles 66 in the peritoneal lining (not indicated). As shown in FIG. 7B, microwave emitter 38 is then used to irradiate the patient's abdomen with weak microwave energy 71.

In yet another application diagrammatically depicted in FIG. 8, a suspension or slurry of metal particles 72 is fed from a syringe 74 into an artery AR having an aneurysm ANM. A magnet may be used to embed the metal particles 72 in the artery's endothelium (not illustrated), particularly in the endothelium of aneurysm ANM. The injection of metal particles 72 and the embedding thereof in the wall of aneurysm ANM may be sufficient to produce clotting in the aneurysm. The clotting is preferably controlled so that blood can still flow through the normal section of the artery AR after treatment. Microwave emitter 38 is optionally used to irradiate the patient with weak microwave energy 76. As discussed above, this additional step will accelerate the scarring of the endothelial tissues and possibly the clotting for selectively occluding aneurysm ANM but not artery AR.

Figure 9:
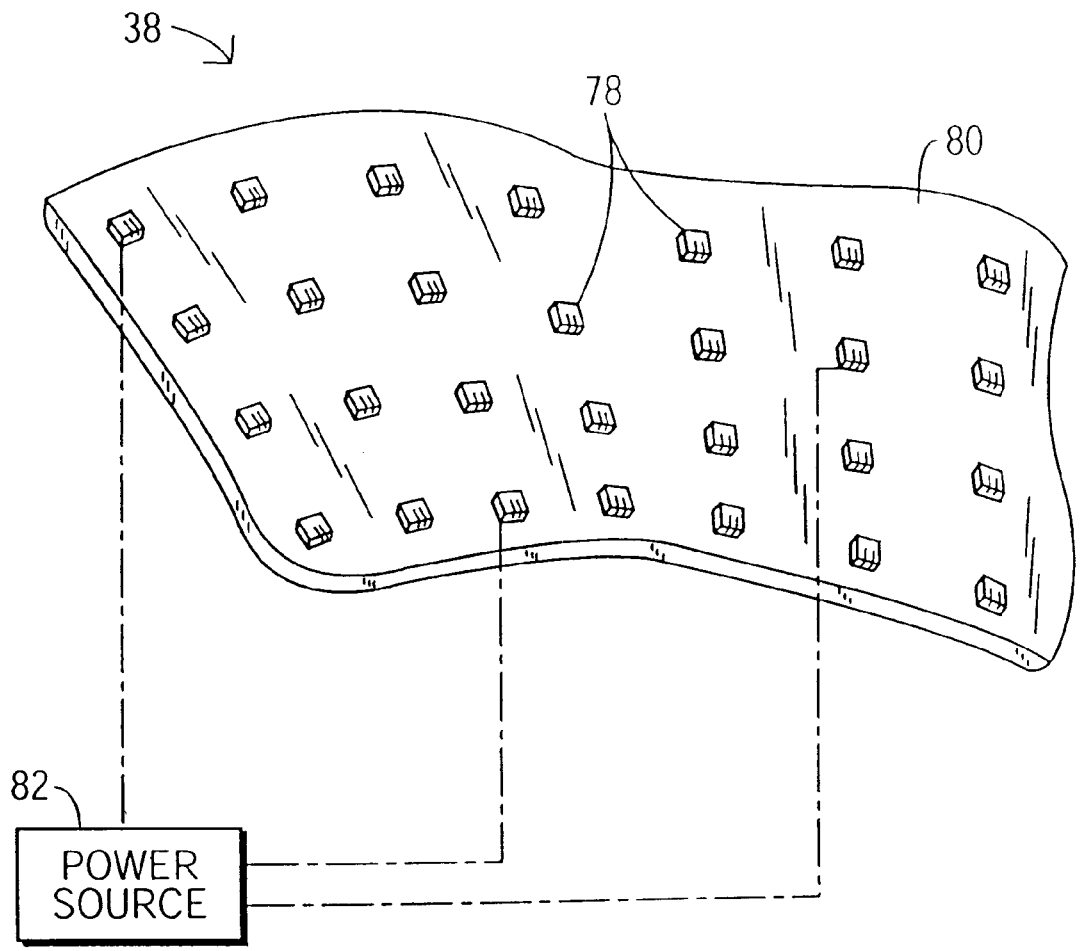
FIG. 9 is a schematic perspective view of a microwave treatment device in accordance with the invention, for use in medical treatment procedures in accordance with the invention.

As illustrated in FIG. 9, microwave emitter 38 may be provided in the form of a plurality of solid state transducers 78 in the nature of light-emitting diodes for generating microwave radiation. Transducers 78 are attached in a spaced array to a flexible substrate 80 which is draped on or over a patient. A power supply 82 is connected to the individual microwave generating transducers 78 for providing electrical energy thereto.

Although the invention has been described in terms of particular embodiments and applications, one of ordinary skill in the art, in light of this teaching, can generate additional embodiments and modifications without departing from the spirit of or exceeding the scope of the claimed invention. For example, magnet 26 may be placed near uterus UT prior to the injection of metal particles 18, rather than afterward. Metal particles 18, 62, 66, and/or 72 may be provided with an irritant coating such as cyanoacrylate to expedite scarring. Other coatings are also possible: growth factor, anti-growth factor, antibiotics, etc.

Accordingly, it is to be understood that the drawings and descriptions herein are proffered by way of example to facilitate comprehension of the invention and should not be construed to limit the scope thereof.

What is claimed is:

1. A sterilization method comprising:
    depositing a plethora of magnetizable metal particles into a uterus of a living female organism; and
    placing a magnet near an external skin surface of the female organism near said uterus to thereby cause at least some of said metal particles to embed in a lining or myometrium of said uterus.

2. The method defined in claim 1 wherein the depositing of said metal particles includes inserting a tubular member through a cervix of the female organism and injecting said metal particles through said tubular member.

3. The method defined in claim 2 wherein said metal particles are suspended in a flowable matrix, the depositing of said metal particles in said uterus including exerting pressure on said flowable matrix to cause said flowable matrix with the suspended metal particles to flow into said uterus.

4. The method defined in claim 3 wherein said tubular member is provided with a balloon, further comprising inflating said balloon after inserting said tubular member through said cervix and prior to injecting of said metal particles through said tubular member, thereby closing said uterus prior to the depositing of said metal particles into said uterus.

5. The method defined in claim 1 wherein said metal particles are suspended in a flowable matrix, the depositing of said metal particles in said uterus including exerting pressure on said flowable matrix to cause said flowable matrix with the suspended metal particles to flow into said uterus.

6. The method defined in claim 1 wherein particles are magnetized prior to the depositing of said metal particles in said uterus.

7. The method defined in claim 1, further comprising emitting microwave radiation into the female organism in a region about said uterus after the embedding of said metal particles in said lining or myometrium.

8. The method defined in claim 1 wherein said metal particles are coated with a biological irritant composition to cause scarring of said lining or myometrium after embedding of said metal particles in said lining or myometrium.

9. A medical treatment method comprising:
    depositing a plethora of magnetizable metal particles into internal tissues of a living organism; and
    emitting microwave radiation into the organism in a region about said internal tissues after the depositing of said metal particles in said internal tissues.

10. The method defined in claim 9 wherein the internal tissues are a lining, the depositing of said metal particles including:
    inserting a tubular member through a skin surface of the organism and into a cavity defined or surrounded by said lining; and
    filling said cavity with a solution or suspension containing said metal particles.

11. The method defined in claim 10 wherein said lining is a peritoneal lining, said cavity being a peritoneal cavity.

12. The method defined in claim 9 wherein the internal tissues are a tumorous growth, the depositing of said metal particles including:
    inserting a hypodermic needle through a skin surface of the organism and into said tumorous growth; and
    injecting said metal particles through said needle into said tumorous growth.

13. The method defined in claim 9 wherein said internal tissues are an aneurysm.

14. The method defined in claim 9 wherein said metal particles are suspended in a flowable matrix, the depositing of said metal particles in said internal tissues including exerting pressure on said flowable matrix to cause said flowable matrix with the suspended metal particles to flow into said internal tissues.

15. The method defined in claim 9 wherein particles are magnetized prior to the depositing of said metal particles in said internal tissues.

16. The method defined in claim 9 wherein said metal particles are coated with a biological irritant composition.

17. A sterilization method comprising:
    inserting a tubular member through a cervix of a female organism;
    thereafter injecting a sclerosing agent into a uterus of the female organism through said tubular member, said sclerosing agent including a plethora of metal particles; and
    acting on said metal particles to embed said metal particles in a lining or myometrium of said uterus.

18. The method defined in claim 17 wherein the acting on said metal particles includes orienting said particles.

19. The method defined in claim 18 wherein the orienting of said metal particles includes applying a magnetic field to said metal particles.

20. The method defined in claim 17, further comprising emitting microwave radiation into the female organism in a region about said uterus after the injecting of said metal particles into said uterus.

21. The method defined in claim 17 wherein said tubular member is provided with a balloon, further comprising inflating said balloon after inserting said tubular member through said cervix and prior to injecting of said sclerosing agent through said tubular member, thereby closing said uterus prior to the injecting of said sclerosing agent into said uterus.

* * * * *